(12) United States Patent
Carpenter

(10) Patent No.: US 8,366,681 B2
(45) Date of Patent: Feb. 5, 2013

(54) HIGH FLOW VOLUME NASAL IRRIGATION DEVICE AND METHOD FOR ALTERNATING PULSATILE AND CONTINUOUS FLUID FLOW

(76) Inventor: Mark Carpenter, White Lake, MI (US)

( * ) Notice: Subject to any disclaimer, the term of this patent is extended or adjusted under 35 U.S.C. 154(b) by 121 days.

(21) Appl. No.: 12/942,634

(22) Filed: Nov. 9, 2010

(65) Prior Publication Data

US 2011/0087188 A1    Apr. 14, 2011

Related U.S. Application Data

(63) Continuation-in-part of application No. 12/941,056, filed on Nov. 6, 2010, now Pat. No. 7,976,529, which is a continuation-in-part of application No. 12/900,792, filed on Oct. 8, 2010.

(60) Provisional application No. 61/278,455, filed on Oct. 8, 2009, provisional application No. 61/280,695, filed on Nov. 9, 2009, provisional application No. 61/337,779, filed on Feb. 12, 2010, provisional application No. 61/280,696, filed on Nov. 9, 2009.

(51) Int. Cl.
*A61M 5/178* (2006.01)

(52) U.S. Cl. ........ 604/212; 604/257; 604/275; 604/514; 222/213; 222/491; 222/494

(58) Field of Classification Search .................... 604/19, 604/37, 48, 70, 73, 93.01, 94.01, 118, 132, 604/150, 153, 181, 183, 185–187, 212–217, 604/247, 257–262, 275–279, 500, 514; 222/212, 222/213, 491–497; 137/540
See application file for complete search history.

(56) References Cited

U.S. PATENT DOCUMENTS

| | | | | |
|---|---|---|---|---|
| 2,360,603 | A * | 10/1944 | Ward | 222/153.04 |
| 3,221,945 | A * | 12/1965 | Davis, Jr. | 222/633 |
| 5,301,846 | A * | 4/1994 | Schmitz | 222/211 |
| 6,669,059 | B2 * | 12/2003 | Mehta | 222/211 |

* cited by examiner

*Primary Examiner* — Kevin C Sirmons
*Assistant Examiner* — Kami A Bosworth
(74) *Attorney, Agent, or Firm* — Lyman H. Moulton, Esq.

(57) ABSTRACT

A high flow volume nasal irrigation device for alternating pulsatile and continuous fluid flow includes a tube comprising a free end and a housing at a second end adjoined to a cap with a coaxial cap nipple. A valve assembly inside the housing comprises a disk-like valve and a plurality of housing standoffs configured to stop the valve but allow a fluid flow in the housing and out the nipple. A cylindrical elastic valve seat is adjoined to the cap nipple and forms a gap with the valve on the standoffs. A spring opposes the valve moving toward the valve seat from the standoffs and assists in returning the valve from the seat to the standoffs and thus with the valve seat creates a periodic pulsatile fluid flow in the nipple in response to a chamber pressure which exceeds a critical chamber pressure threshold.

19 Claims, 7 Drawing Sheets

HIGH FLOW VOLUME NASAL IRRIGATION DEVICE AND METHOD FOR ALTERNATING PULSATILE AND CONTINUOUS FLUID FLOW

CROSS-REFERENCE TO RELATED APPLICATIONS

This application is a continuation-in-part of U.S. patent application Ser. No. 12/941,056 entitled A High Flow Volume Nasal Irrigation Device and Method for Alternating Pulsatile and Continuous Fluid Flow, filed for Mark Carpenter on the 6 Nov. 2010 now U.S. Pat. No. 7,976,529 which itself is a continuation-in-part of Ser. No. 12/900,792 entitled A High Flow Volume Nasal Irrigation Device and Method for Alternating Pulsatile and Continuous Fluid Flow, filed for Mark Carpenter on Oct. 8, 2010 which itself claims the benefit of the priority date of earlier filed U.S. Provisional Patent Application Ser. No. 61/278,455 filed Oct. 8, 2009 and entitled High Volume Nasal Irrigation Device with Pulsatile Flow, also for Mark Carpenter, each incorporated herein by reference in its entirety. This application also incorporates herein by reference in its entirety each earlier filed U.S. Provisional Patent Application Ser. No. 61/280,695 entitled High Volume Nasal Irrigation Device with Pulsatile Flow—Version 2, filed Nov. 9, 2009, for Mark Carpenter, U.S. Provisional Patent Application Ser. No. 61/337,779 entitled High Volume Nasal Irrigation Device with Pulsatile Flow—Version 2b, filed Feb. 12, 2010, for Mark Carpenter and U.S. Provisional Patent Application Ser. No. 61/280,696 entitled High Volume Nasal Irrigation Device with Pulsatile Flow—Version 3, filed Nov. 9, 2009, also for Mark Carpenter.

BACKGROUND AND FIELD OF INVENTION

Flood irrigation differs significantly from the practice of inhaling an atomized mist into the nose. During flood irrigation, the vast majority (>95%) of fluid taken in is expelled immediately (or shortly thereafter) after the contaminants have been rinsed out. Rinsing with flood irrigation is commonly performed by ingesting the liquid solution into one nostril and concurrently expelling the solution from the other nostril. Alternately, flood irrigation is sometimes performed by ingesting the liquid solution into both nostrils simultaneously and having the excess flow to the mouth. Flood irrigation has been demonstrated to be more effective than mist for the distribution of medications and the physical rinsing of the mucus membranes of the nose and sinuses. A user of nasal flood irrigation may typically use the technique once or twice per day as opposed to a user applying a mist several to many times a day.

The use of flood irrigation to cleanse, soothe and rehabilitate nasal and sinus passages has a long history which probably began with the practice of intentional inhalation of sea water from cupped hands. Later devices such as the Neti Pot made the practice more practical. Today there is a wide array of devices and technologies to facilitate the rinsing by flood irrigation of the nasal passages and sinus cavities. Investigation of prior art shows that the number of relevant devices and techniques has grown at an increasing rate in recent decades and in particular during the last ten years. This growth in technology has paralleled the increasing popularity of the practice as the technology has become more effective and as the benefits of the practice have become more appreciated.

Within the field of flood irrigation for nasal rinsing there are developments in the liquid solutions being used and there are developments in the device which delivers the liquid stream. The liquid delivery devices for nasal flood irrigation may be generally divided into two major commercial categories—a) simple devices which dispense a continuous low pressure stream of fluid from a squeeze bottle, deformable bulb, bellows container, shower head connection, gravity feed, etc., and b) devices which use a motorized pump or other complex and expensive electromechanical apparatus to provide a pulsating stream of fluid. Both categories of device have advantages and disadvantages.

The devices which dispense a continuous low pressure stream of irrigant typically are very low in cost and may have advantageously high flow rate capability. Unfortunately, these devices offer a less than optimal cleaning ability due to the tendency of the continuous stream to form laminar flow paths across the surfaces to be rinsed and due to the surfaces not being deformed and agitated by the smooth flow stream. These continuous stream devices are also ineffectual in projecting liquid medications or irrigants into sinus cavities because the closed end cavities require time varying pressures to cause fluid entry. They also fail to rehabilitate nasal cilia which have lost motility.

The pulsating electromechanical devices have the advantages of causing a much more turbulent scouring flow with high shear stress gradients along the surfaces, causing a mixing action to reduce surface based concentration gradients and deformations of the surfaces being rinsed (for flexible surfaces) and healthy movement of the nasal cilia. Pulsating electromechanical devices unfortunately offer a less than optimal flow rate. Additionally, the pulsatile electromechanical devices are significantly more complex and costly, with purchase cost approximately ten times that of a squeeze bottle irrigator. This high cost prevents many potential users from purchasing them and does not favor the periodic disposal of the device which is necessary to avoid colonization by bacteria and molds.

SUMMARY OF THE INVENTION

A high flow volume nasal irrigation device for alternating pulsatile and continuous fluid flow is disclosed which includes a squeeze bottle configured to elastically deform in response to a manually applied pressure on the bottle and thus pressurize the liquid and chamber therein. A removable cap is disposed on the squeeze bottle open end and comprises a nipple configured to a typical user's nostril. A tube conveys a liquid from a reservoir in a chamber under an elevated chamber pressure to a lower pressure outside the chamber. The tube comprises a free end and a housing at a second end adjoined to a cap with a coaxial cap nipple. A valve assembly proximal the tube inside the housing comprises a disk-like valve and a plurality of housing standoffs configured to stop the valve but allow a fluid flow in the housing and out the nipple. An outer periphery of the valve and the housing forms an area for the fluid flow. A cylindrical elastic valve seat is adjoined to the cap nipple and forms a gap with the valve on the standoffs. The valve seat has an inside diameter smaller than the valve and a restoring force in opposition to a force applied by the valve on the seat in response to a fluid pressure. A spring opposes the valve moving toward the valve seat from the standoffs and assists in returning the valve from the seat to the standoffs and thus with the valve seat create a periodic pulsatile fluid flow in the nipple in response to a chamber pressure which exceeds a critical chamber threshold.

A method for squeezing a deformable bottle containing a fluid and thereby creating a chamber pressure urging a fluid flow through a dip tube and out a bottle cap orifice placed adjacent at least one of a user's nostrils includes stopping fluid flow by compressing a disk-like valve against a cylindrical elastic valve seat and a coaxial spring in response to a compressing force generated by a fluid pressure. The method also includes restarting fluid flow in response to a rebounding of the valve seat and spring and thus propelling the valve away from the seat toward a plurality of standoffs. The disclosed method therefore provides high flow volume pulsatile fluid flow nasal irrigation through the cap orifice, the pulsatile flow in response to the fluid flow stopping and restarting in a period related to a pressure threshold constant. The disclosed method further may comprise squeezing the bottle gently to a chamber pressure below the pressure threshold constant to eject a continuous stream of the fluid from the bottle and squeezing the bottle vigorously to a chamber pressure above the pressure threshold constant to eject an oscillatory pulsating stream of the fluid from the bottle. The method may also further comprise alternating between ejecting a continuous fluid stream and a pulsating fluid stream by alternating the respective gentle and vigorous squeezings.

Throughout the description, similar reference numbers may be used to identify similar elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

The disclosed device is capable of providing a continuous flow rate from gentle to very high flow and alternatively at the control of the user, capable of generating a strong pulsatile flow stream at a variable intensity, amplitude and frequency. Pulsating components of the disclosure may be placed between the dip tube and the cap of a conventional bottle type nasal irrigation device. The components explained in detail below may be selected to cause a valve therein to rapidly and cyclically generate a pulsatile fluid flow from the device.

Figure 1:
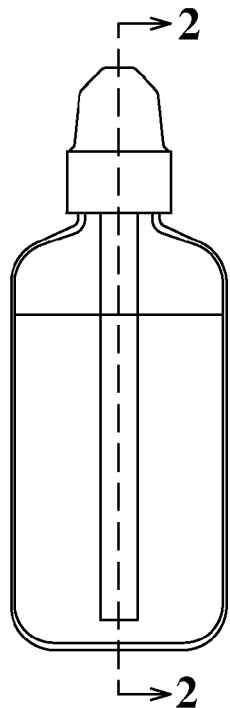
FIG. 1 is a side elevational view of a high flow volume nasal irrigation device for alternating pulsatile and continuous fluid flow in accordance with an embodiment of the present disclosure.

FIG. 1 is a side elevational view of a high flow volume nasal irrigation device for alternating pulsatile and continuous fluid flow in accordance with an embodiment of the present disclosure. A squeeze bottle portion of the device as depicted is transparent. Alternate embodiments may include any combination of transparent, translucent and opaque elements. A cross section 2-2 taken through the diameter of the device is illustrated in FIG. 2 which follows.

Figure 2:
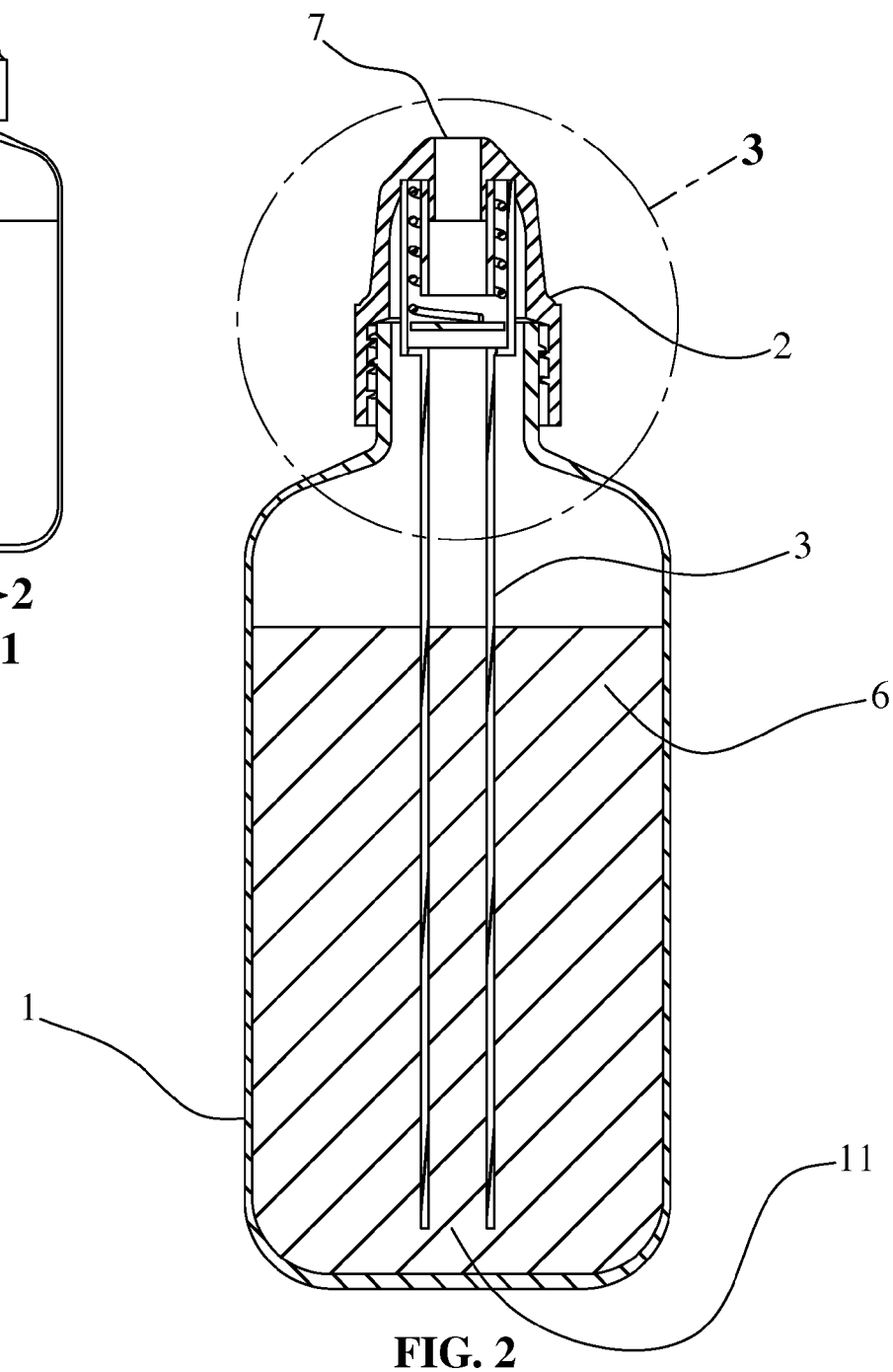
FIG. 2 is a cross-sectional view of the device of FIG. 1 taken through its diameter 2-2 in accordance with an embodiment of the present disclosure.

FIG. 2 is a cross-sectional view of the device of FIG. 1 taken through its diameter 2-2 in accordance with an embodiment of the present disclosure. The device as depicted may include a deformable chamber or bottle 1, a removable cap 2 and a dip tube 3, a reservoir of fluid 6, a cap orifice 7 and an inlet 11. The fluid 6 may be an isotonic therapeutic fluid for bodily lavage or specifically formulated for nasal irrigation. A fluid level may vary in the bottle but should at least be sufficient to submerge the dip tube inlet 11 in order that the fluid 6 be propelled up the tube 3 toward the pulsatile components when the bottle 1 is squeezed. The alternating short and long dashed circle labeled in bold 3 is detailed in close-up in the following figure FIG. 3.

Figure 3:
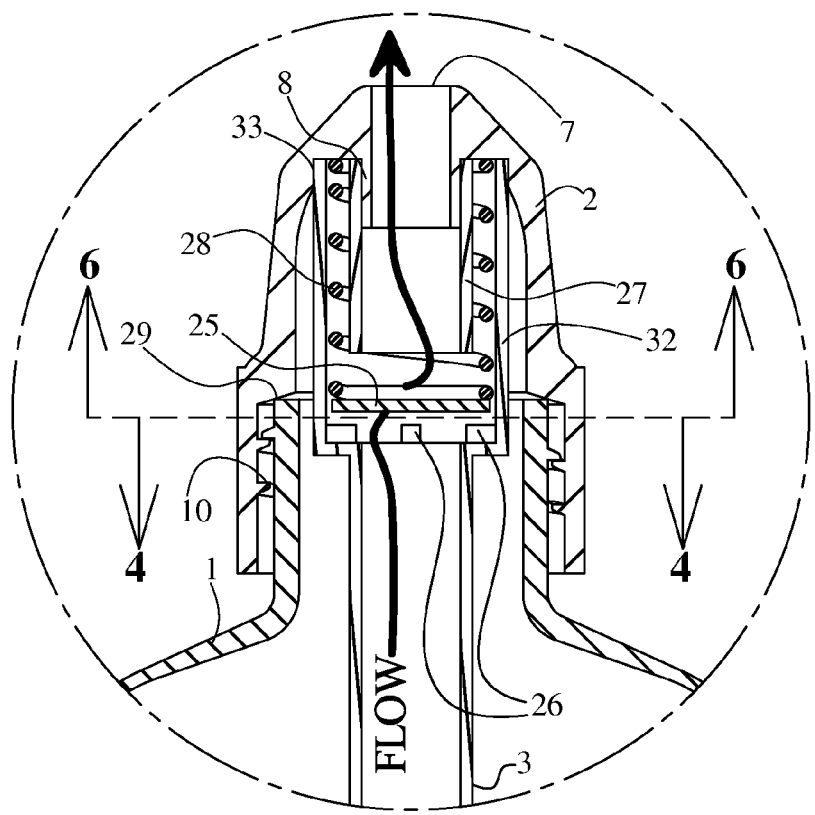
FIG. 3 is a detailed view of the cross-section of FIG. 2 in accordance with an embodiment of the present disclosure.

FIG. 3 is a detailed view of the cross-section of FIG. 2 in accordance with an embodiment of the present disclosure. The depiction further includes the nipple extension 8, the threaded connection 10, the substantially flat and disk-like valve 25, the housing standoffs 26, the valve seat 27, the spring 28, the cap stop 29, the housing 32 and the housing to cap seal 33.

The squeeze bottle 1 is configured to elastically deform in response to a manually applied pressure on the bottle 1 and thus pressurize the liquid 6 and the chamber therein. The squeeze bottle 1 is designed and may be made to elastically deform in response to a manual pressure from a user. The squeeze bottle 1 may comprise an open end and an interior. The squeeze bottle 1 may also be comprised of an elastic thin-wall LDPE (low-density polyethylene) material in order to minimize the squeeze pressure needed to create the pulsatile flow in the tube 3. The squeeze bottle 1 may be configured to fit comfortably into the grasp of an average person and be deformed in response to an average person's squeezing grip. The squeeze bottle 1 therefore may also elastically resume its original shape in preparation for repeated filling and additional use.

A dip tube 3 extends from near the bottom of the bottle and conveys the liquid 6 from a reservoir in the chamber or bottle under an elevated chamber pressure to a lower pressure outside the chamber. The tube 3 comprises an inlet 11 at the free end and a housing 32 at a second end adjoined to the cap 2 with a seal 33. The dip tube 3 may comprise semi-rigid materials or comprise a thick wall material to give it semi-rigid properties. The tube may also comprise a 6 mm (0.24 inches) nominal inside diameter and be no smaller than 3 mm (0.12 inches) in diameter and no greater than 8 mm (0.32 inches) in diameter. The housing may be an enlarged portion of the tube to accommodate assembly of the pulsatile components therein or the housing may share the same diameter with the tube depending on the diameter of the components therein.

A removable cap 2 is disposed on the squeeze bottle open end and comprises a nipple configured to a typical user's nostril. The cap 2 may also comprise a threaded inside diameter 10 corresponding to the outside threaded diameter of the squeeze bottle 1 opening. The nipple includes an orifice 7 and an extension 8. A valve assembly proximal the tube 3 inside the housing 32 comprises a disk-like valve 25 and at least three housing standoffs 26 configured to stop the valve 25 but allow a fluid flow in the housing 32 and out the nipple. An area between the outer periphery of the valve 25 and the housing 32 forms an area for the fluid flow.

A cylindrical elastic and resilient valve seat 27 is adjoined to the cap nipple extension 8 and forms a gap with the valve 25 on the standoffs 26. The valve seat 27 has an inside diameter smaller than the valve 25 and a restoring force in opposition to a force applied by the valve 25 on the seat 27 in response to a fluid pressure. A compression of the valve seat is approximately 20 percent its uncompressed length. The valve seat may also comprise helically alternating ridges and grooves to facilitate the oscillatory movement and to accommodate a spirally wound spring in the grooves thereof.

A spring 28 biases the valve into contact with the housing standoffs which hold the valve at a distance from the housing surface. The spring 28 therefore opposes the valve 25 moving toward the valve seat 27 from the standoffs 26 and assists in returning the valve 25 from the seat 27 to the standoffs 26 and thus with the valve seat 27 creates a periodic pulsatile fluid flow in the nipple in response to a chamber pressure which exceeds a critical chamber threshold. The critical chamber pressure is a chamber pressure which causes fluid flow through the housing sufficient to move the valve against the spring and off from the standoffs and into contact with the valve seat.

Figure 4A:
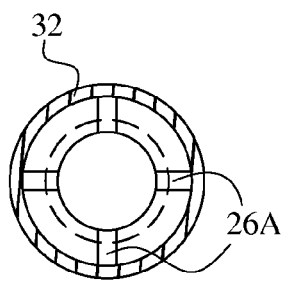
FIG. 4A is a cross-sectional view of a first housing taken through the section 4-4 depicting radial housing standoffs to stop the valve in accordance with an embodiment of the present disclosure.

The valve seat and the spring store mechanical energy when in a compressed configuration and return the stored mechanical energy and momentarily reverse the fluid flow as the valve moves back to the standoffs in a recoil and restore configuration. A frequency of the pulsatile fluid flow is configurable as a function of an area of the fluid flow passage in the housing and out the nipple, the area and mass of the disk, a valve seat spring rate and a spring rate of the spring FIG. 4A is a cross-sectional view of a first housing taken through the section 4-4 depicting radial housing standoffs to stop the valve in accordance with an embodiment of the present disclosure. Radial housing standoffs 26A extend rib-like from an inner wall of the housing and across a floor of the housing created by a flanging of the housing from the tube. In embodiments where smaller pulsatile components do not require an enlarged housing and there is no housing floor, the standoffs may protrude away from the inside wall of the tube to stop the valve from falling further therein. Three or more standoffs allow fluid to flow underneath the valve between the standoffs and around the circumference of the valve (also known as its periphery) and through the housing and out the nipple orifice. Therefore, there is an area between the valve and the housing for fluid flow that is further shown and explained in FIG. 5 and FIG. 6 below.

Figure 4B:
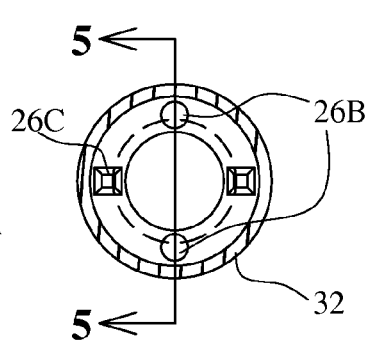
FIG. 4B is a cross-sectional view of a second housing taken through the section 4-4 depicting cylindrical post and pyramidal housing standoffs to stop the valve in accordance with an embodiment of the present disclosure.

FIG. 4B is a cross-sectional view of a second housing taken through the section 4-4 depicting cylindrical post and pyramidal housing standoffs to stop the valve in accordance with an embodiment of the present disclosure. Cylindrical post standoffs 26B, conical standoffs (not depicted) and pyramidal standoffs 26C all support the valve from the floor of the housing so that fluid may flow from the tube into the housing and out the nipple regardless of the position of the valve as long as it is not on the valve seat.

Figure 5:
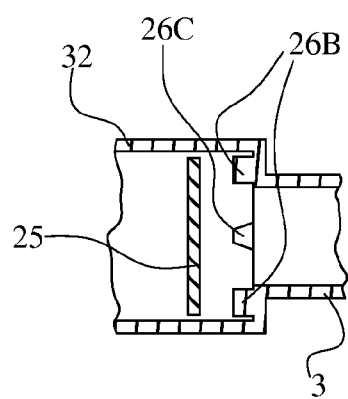
FIG. 5 is a cross-sectional view of FIG. 4B taken through the section 5-5 in accordance with an embodiment of the present disclosure.

FIG. 5 is a cross-sectional view of FIG. 4B taken through the section 5-5 in accordance with an embodiment of the present disclosure. The tube 3 flanges out to create the housing 32 to accommodate the valve 25 and the other components of the device. At the point where the tube flanges out into the housing, standoffs or projections as shown (cylindrical posts 26B and pyramids 26C) extend from a floor of the housing to prevent the valve from shutting off fluid flow from the tube into the housing. Fluid flow is therefore only blocked when the valve sits on the valve seat (not shown).

Embodiments of the disclosed device also provide non-pulsating continuous stream irrigation if the velocity of the fluid flow is maintained below a critical level initiating pulsation. The flow rate of this continuous stream may be controlled by the user over a wide range. If desired by the user, the disclosed device may produce a continuous stream flow rate which is significantly higher than the time averaged flow rate of the device in pulsation mode.

When the disclosed device is operated in the pulsation mode, aka pulsation state, the disclosed pulse generating mechanism may act as a flow control to maintain or even reduce flow in response to increases in bottle or chamber pressure beyond that required to initiate pulsation. With the device in pulsatile mode, increases in squeeze pressure from the user may cause an increase in pulsation amplitude while regulating flow rate to a safe and effective level.

Figure 6A:
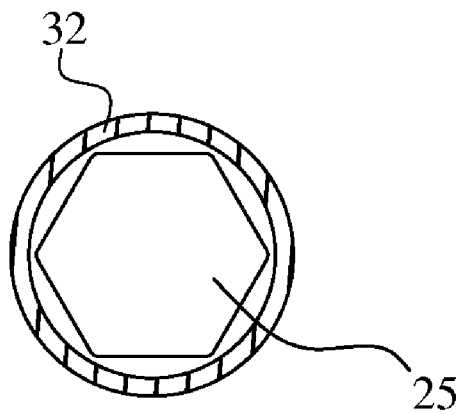
FIG. 6A is a depiction of a first disk-like valve having a polygonal circumferential profile in accordance with an embodiment of the present disclosure.

FIG. 6A is a depiction of a first disk-like valve having a polygonal circumferential profile in accordance with an embodiment of the present disclosure. The valve may be a thin and rigid impermeable disk-like geometry having a selected mass for pulsatile operation. Fluid flow may occur around the polygonal valve 25 and between the vertices of the hexagonal valve specifically and an inside wall of the cylindrical housing 32. Other polygonal circumferential profiles may also accommodate fluid flow between the valve 25 and the housing 32 such as higher order octagonal shapes.

Figure 6B:
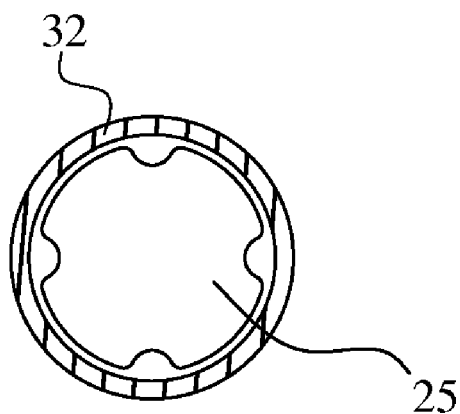
FIG. 6B is a depiction of a second disk-like valve having a scalloped circumferential profile in accordance with an embodiment of the present disclosure.

FIG. 6B is a depiction of a second disk-like valve having a scalloped circumferential profile in accordance with an embodiment of the present disclosure. The scalloped cutaways comprise a continuous series of semicircle segments on the circumferential periphery of the valve and permit fluid flow around the valve and between the valve and the housing. Any higher number of cutaways or any cutaway geometry may also allow fluid flow through the housing around the valve in embodiments of the present disclosure.

Figure 6C:
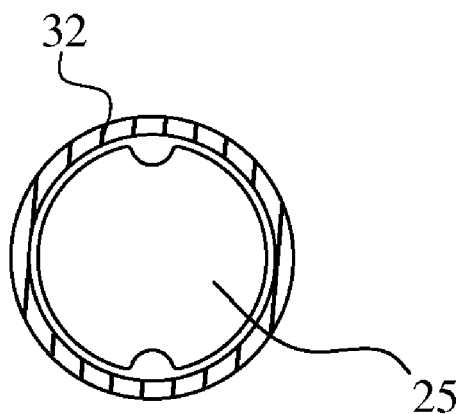
FIG. 6C is a depiction of a third disk-like valve having a fluted circumferential profile in accordance with an embodiment of the present disclosure.

FIG. 6C is a depiction of a third disk-like valve having a fluted circumferential profile in accordance with an embodiment of the present disclosure. A fluted or vertical rounded groove in the valve circumference allows fluid flow around the valve and through the housing. Parallel flutes may also provide grooves for guides in the housing (not shown) to keep the valve positioned orthogonal to the direction of fluid flow in embodiments where the valve is not attached directly to the spring.

Additional embodiments of the high flow volume nasal irrigation device may comprise the tube, the housing, the disk, the valve and the elastic valve seat comprising at least one of an arcuate cross section and any polygonal cross section. In other words, the housing for the valve of FIG. 6A may also be hexagonal to accommodate movement of the valve between the standoffs and the valve seat. Cutaways or scallops and flutes on the vertices of polygonal valves may therefore accommodate fluid flow around the valve and through the housing.

Embodiments of the valve comprise a nominal circumferential side wall and a top surface and a bottom surface, the top and bottom surfaces may be configured in at least one of a convex, a concave and a flat surface. A convex upper surface on the valve may better retain the spring. A concave surface on a bottom valve surface facing the standoffs may increase the surface area of the valve available for lifting the valve from the standoffs and propel it toward the valve seat.

Embodiments of the disclosed device may include a second reservoir in accordance with an embodiment of the present disclosure. A second reservoir of liquid may be located at a height above the user and the first reservoir as explained further below. A valve may be further configured in the fluid path from the second reservoir to the chamber to control the flow of fluid into the chamber.

In an embodiment of the disclosed high flow volume nasal irrigation device, at least one of the bottle 1, the cap 2 and the dip tube 3 may be comprised of a purple material, a purple coloring and/or a purple covering configured as a color code for consumers to identify and differentiate the device for purchase and proper application. Since the advantages of the present disclosure distinctly set it apart from other nasal irrigation devices on the market, consumers will naturally want to continue their exclusive purchase of the disclosed device they have come to trust and rely upon for specific medicinal and hygienic applications. The color code as claimed herein allows consumers to avoid mistakes in purchasing other less advantageous and applicable nasal irrigators and to consistently identify and purchase the disclosed device by the purple color code.

Fluid flow in the disclosed device may be initiated by a manual pressure applied to the bottle. Fluid velocity quickly builds as fluid flows through the dip tube in response to the chamber pressure from the squeeze. As fluid flow increases, a pressure differential develops across the valve due to the restriction in the flow path that exists between the outside diameter of the valve and the inside diameter of the housing. When the pressure differential acting on the large faces of the valve generates a force sufficient to overcome the force of the spring, the valve is lifted off the standoffs. As the valve rises from its static position there is little change in the overall resistance to fluid flow as the area between the edges of the valve and the housing remains constant. The flow rate continues to increase as the pressure differential along the flow path accelerates the fluid which was initially at rest. The valve will be raised ever higher until its upper surface is brought into contact with the lower end surface of the elastic valve seat.

The valve making contact with the valve seat may cause a sudden closure of the flow path and a nearly complete stoppage of fluid flow through the device. The sudden closure generates pressure changes on both sides of the valve as the column of rapidly flowing fluid is decelerated. Below the valve, the deadheading of the fluid between liquid intake opening 11 and the valve will cause a pronounced increase in pressure to act on the lower surface of the valve. Above the valve, all of the fluid between the valve and the dispensing orifice will be decelerated to cause a sudden reduction in pressure. The increased force generated by these two differential pressures will cause the elastic valve seat to be axially compressed upward. During this elastic compression, kinetic energy from the moving fluid will be stored as potential energy in the elastic valve seat. After deformation of the elastic valve seat, flow will stop completely and potential energy will begin to be returned to kinetic energy. Flow will be temporarily reversed as the valve is pushed downward by the elastic valve seat and spring. Once the valve falls beyond the end of the fully extended valve seat, it continues downward propelled by inertia, gravity, spring force and some fluid forces. When the valve reaches the housing standoffs, it temporarily stops in its initial position and the cycle begins again. These activities within the device will continue to repeat causing pulsatile flow until the liquid is expended or until the user chooses to relax pressure on the bottle.

Figure 7:
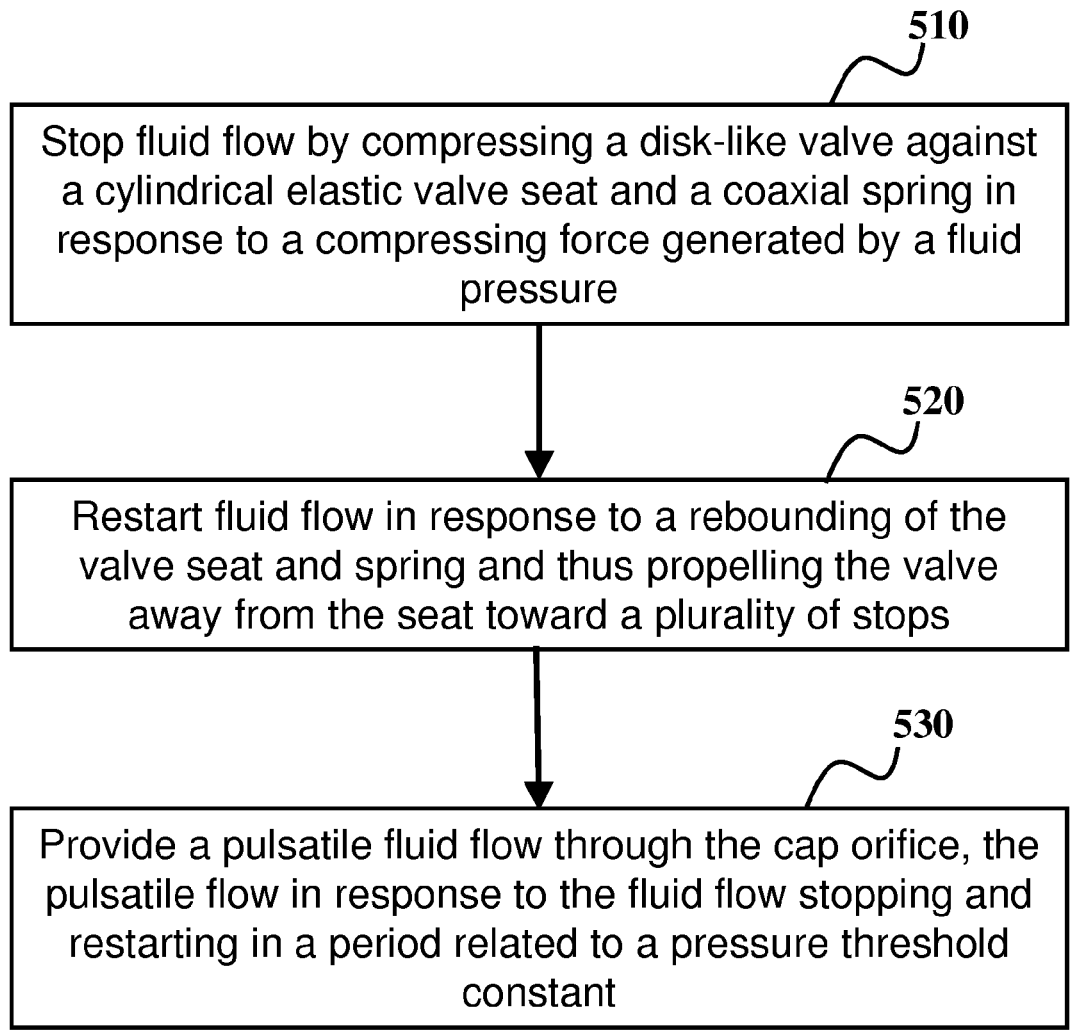
FIG. 7 is a flow chart of a method of alternating pulsatile and continuous fluid flow through a high flow volume nasal irrigation device in accordance with an embodiment of the present disclosure.

FIG. 7 is a flow chart of a method of ejecting a high flow volume pulsatile nasal irrigation rinse in accordance with an embodiment of the present disclosure. Embodiments may include methods of ejecting a high flow volume nasal irrigation rinse by squeezing a deformable bottle containing a liquid and thereby urging the liquid through a dip tube in the bottle out a bottle cap orifice placed adjacent at least one of a user's nostrils. One embodied method includes 510 stopping fluid flow by compressing a disk-like valve against a cylindrical elastic valve seat and a coaxial spring in response to a compressing force generated by a fluid pressure. Stopping fluid flow further increases a fluid pressure acting on the valve and compresses the valve into the valve seat. The method also includes 520 restarting fluid flow in response to a rebounding of the valve seat and spring and thus propelling the valve away from the seat toward a plurality of standoffs. The method further includes 530 providing a pulsatile fluid flow through the cap orifice, the pulsatile flow in response to the fluid flow stopping and restarting in a period related to a pressure threshold constant.

Figure 8:
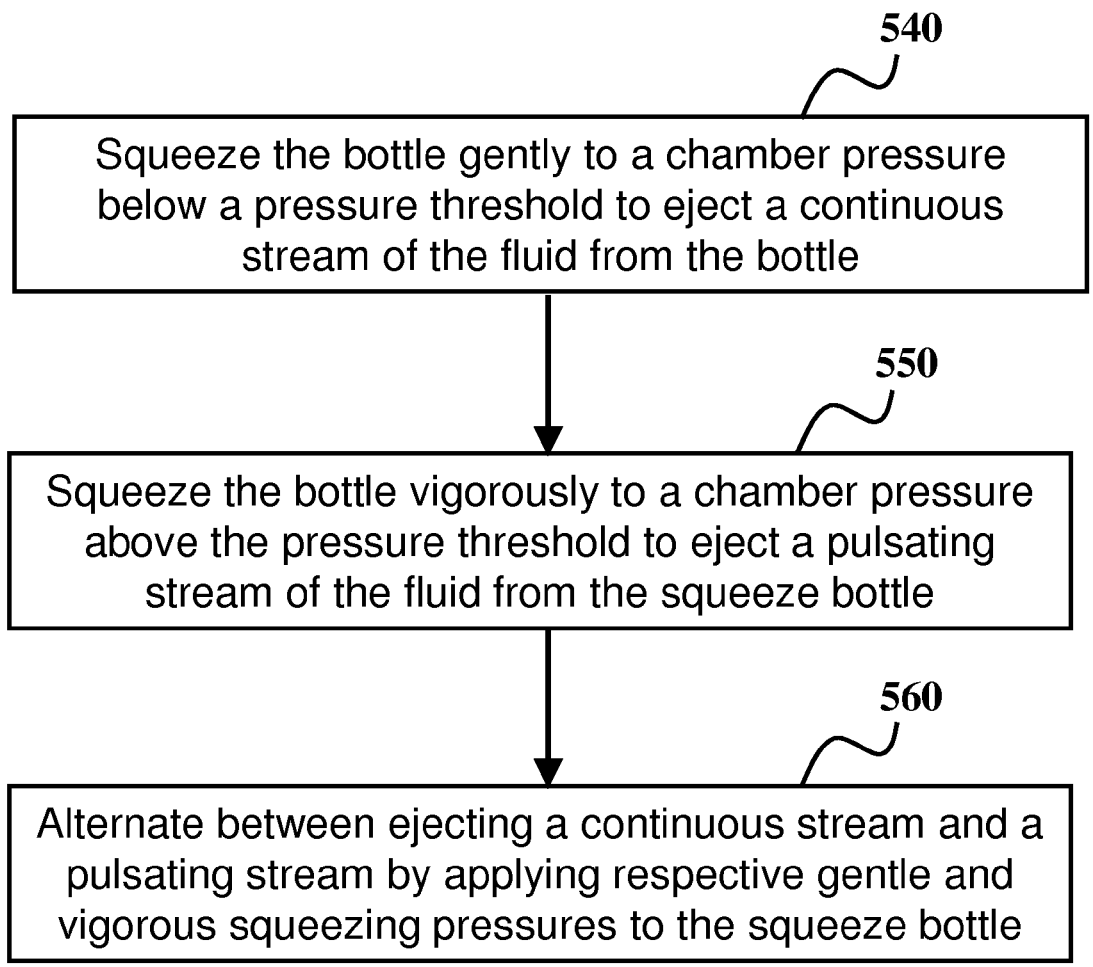
FIG. 8 is a flow chart of a method comprising additional steps for alternating pulsatile and continuous flow through a high flow volume nasal irrigation device in accordance with an embodiment of the present disclosure.

FIG. 8 is a flow chart of a method comprising additional steps for alternating pulsatile and continuous flow through a high flow volume nasal irrigation device in accordance with an embodiment of the present disclosure. An embodiment of the method of ejecting a high flow volume nasal irrigation rinse of above, further comprises 540 squeezing the bottle gently to a chamber pressure below a pressure threshold to eject a continuous stream of the fluid from the bottle and 550 squeezing the bottle vigorously to a chamber pressure above the pressure threshold to eject a pulsating stream of the fluid from the squeeze bottle. The disclosed embodiment further includes 560 alternating between ejecting a continuous stream and a pulsating stream by applying respective gentle and firm or vigorous squeezing pressures to the squeeze bottle.

Figure 9:
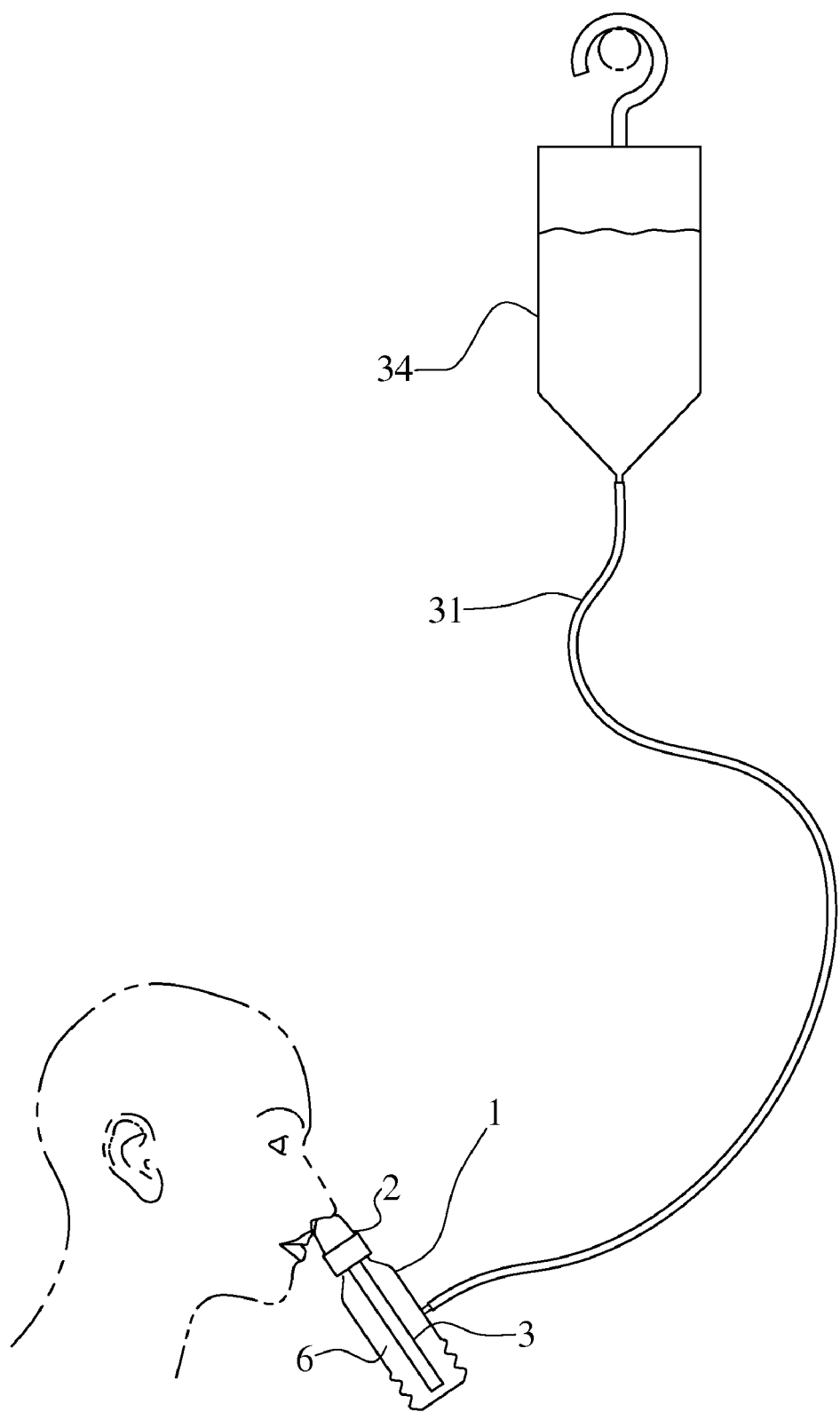
FIG. 9 is a depiction of a high flow volume nasal irrigation device for alternating pulsatile and continuous fluid flow including a second reservoir of liquid in accordance with an embodiment of the present disclosure.

FIG. 9 is a depiction of a high flow volume nasal irrigation device for alternating pulsatile and continuous fluid flow including a second reservoir of liquid in accordance with an embodiment of the present disclosure. The first reservoir of liquid 6 in the bottle 1 and the second reservoir 34 may be configured to create a pressure from a volume of liquid therein at a predetermined height. The disclosed embodiment may also include a conveyance tube 31 arranged to convey fluid from the second reservoir 34 into the bottle or chamber 1 through an effective column of fluid. This embodiment and like embodiments may therefore preclude a user squeezing the bottle 1 since the derived pressure necessary to induce pulsatile flow through the cap 2 into a user's nostril is created by the second reservoir 34 and the column of liquid through the conveyance tube 31.

Figure 10:
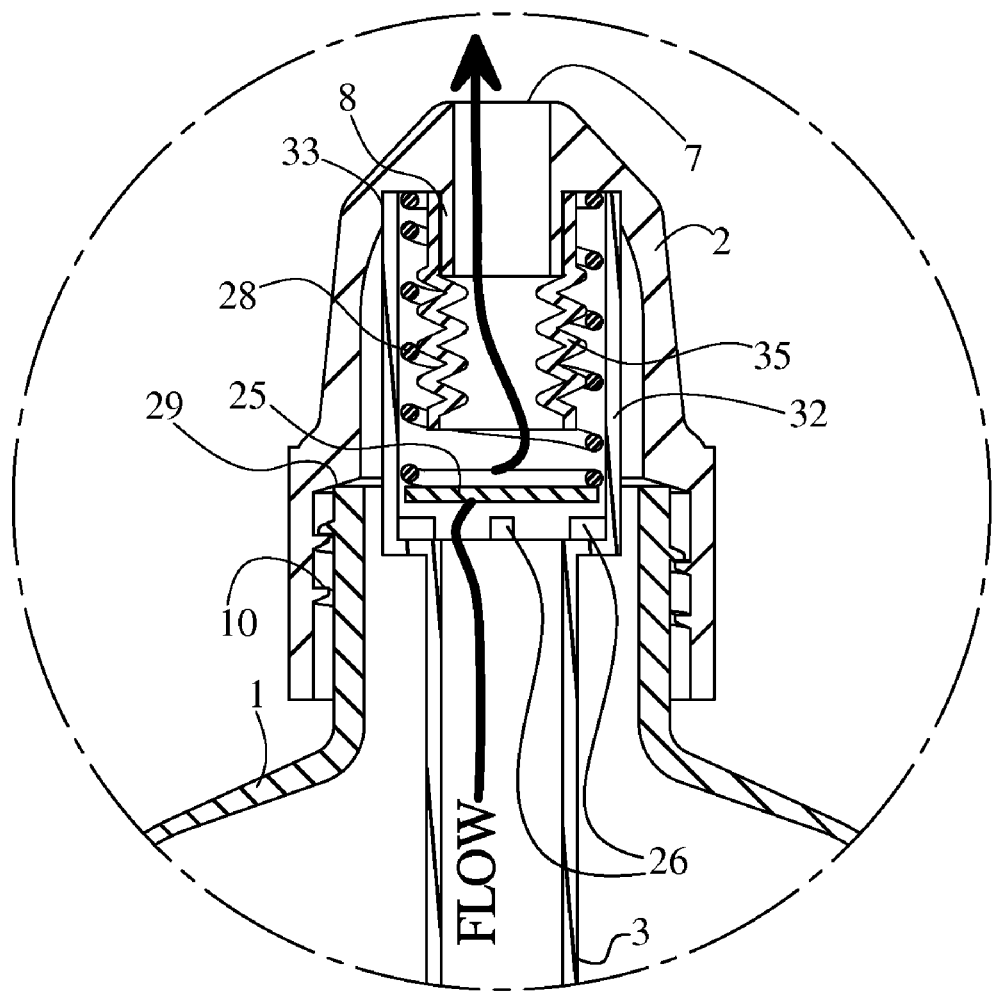
FIG. 10 is a detailed view of a cross-section similar to the cross sectional view of FIG. 3 with the addition of a bellows valve seat in accordance with an embodiment of the present disclosure.

FIG. 10 is a detailed view of a cross-section similar to the cross sectional view of FIG. 3 with the addition of a bellows valve seat in accordance with an embodiment of the present disclosure. The valve seat may be configured as depicted in a cylindrical bellows-like construction to facilitate oscillating motion and the pulsatile fluid flow through the nipple orifice. Reference numbers shown are the same or similar to those of FIG. 3 with the addition of the bellows 35.

Embodiments of the disclosure include configuring the pressure threshold constant as a function of at least an area of the fluid flow passage through the tube and past the valve, the area and mass of the valve and a spring installed force and a spring rate. Embodiments of the disclosure also include varying the pressure threshold constant by varying at least one of an area of the fluid flow passage through the tube and past the valve, the area and mass of the valve and a spring installed force and a spring rate. Embodiments further include varying an oscillatory frequency and period of a pulsating stream of fluid ejected from the bottle by varying the manual pressure applied to the squeeze bottle.

In support of the above operation and procedure of the disclosed nasal irrigation device, a user may remove the cap, including the dip tube, from the bottle. The user fills the squeeze bottle to a desired level with either previously prepared rinsing solution or with water preferably at body temperature. If filled with water, the user may add a pre-packaged solute resulting in the desired solution when agitated. After screwing the cap on the bottle, the user may position herself or himself over a basin and align and lightly press the cap orifice against one nostril to obtain a seal with the nostril. The user then applies a respective squeeze pressure to the bottle in order to force a continuous or pulsatile fluid flow into the nose and sinus cavities. The user may perform the procedure on the other nostril blowing his or her nose between sequences.

The disclosed nasal irrigation device may be operated at a nominal oscillatory frequency of 10 Hertz to 20 Hertz by varying the manual chamber or squeeze pressure and the maintenance pressure applied to the squeeze bottle. Therefore, the operating frequency controlled by the user may resonate with the natural beat of the nasal cilia. The user may also generate other pulsatile frequencies operating the disclosed device as needed to achieve medicinal and hygienic results.

The disclosed device may also be used as a general purpose lavage in the therapeutic washing of bodily orifices, organs, wounds and abrasions. Advantages of the disclosed sinus and nasal irrigation device include the ability to provide the best benefits of the simple squeeze bottle irrigators and simultaneously provide the best benefits of the complex electromechanical irrigators while avoiding any of the negatives of either of these classes of devices. Specifically, advantages of the disclosed device include: a very low manufacturing cost, comparable to that of a squeeze bottle irrigator, a very low part count—requires only 3 to 4 separate manufactured components, continuous stream or pulsatile irrigation from the same device without need for the user to reconfigure the device, a continuous stream which the user may vary in strength from minimal flow up to a flow rate which equals or exceeds currently available irrigation devices, a pulsatile stream which the user may vary in strength from weak through a pulsation amplitude which exceeds that of currently available pulsatile irrigation devices, improved cleansing action, improved distribution of medicated solutions, improved ability to project solution into sinus cavities, improved ability to stimulate nasal cilia, inherent flow regulation which allows the user to squeeze firmly without risking exposure to harmful flow rates, simple and intuitive operation with no external controls, no need for power cords, hoses, or other encumbrances allowing safe and easy use while effectively directing the flow stream into the correct areas of the nose.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

While the forgoing examples are illustrative of the principles of the present disclosure in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the disclosure be limited, except as by the specification and claims set forth herein.

What is claimed is:

1. A high flow volume nasal irrigation device, comprising:
a) a tube configured to convey a liquid from a reservoir in a chamber under an elevated chamber pressure to a lower pressure outside the chamber, the tube comprising a free end and a housing at a second end adjoined to a cap with a coaxial cap nipple;
b) a valve assembly proximal the tube inside the housing, the valve assembly comprising a disk-like valve and a plurality of housing standoffs configured to stop the valve but allow a fluid flow in the housing and out the cap nipple, an outer periphery of the valve and the housing forming an area for the fluid flow;
c) a cylindrical elastic valve seat adjoined to the cap nipple and forming a gap with the valve on the standoffs, the valve seat having an inside diameter smaller than the valve and a restoring force in opposition to a force applied by the valve on the valve seat in response to a fluid pressure; and
d) a spring configured to oppose the valve moving toward the valve seat from the standoffs and assist in returning the valve from the valve seat to the standoffs and thus with the valve seat create a periodic pulsatile fluid flow in the cap nipple in response to a chamber pressure which exceeds a critical chamber pressure threshold.

2. The high flow volume nasal irrigation device of claim 1, wherein the disk-like valve is substantially flat and comprises at least one of a scalloped periphery, a fluted periphery and a polygonal circumferential profile.

3. The high flow volume nasal irrigation device of claim 1, wherein the plurality of housing standoffs configured to stop the valve comprise at least 3 standoffs each projecting away from at least one of a housing floor and a housing inner wall.

4. The high flow volume nasal irrigation device of claim 1, wherein the critical chamber pressure threshold is a chamber pressure which causes fluid flow through the housing sufficient to move the valve against the spring and off from the standoffs and into contact with the valve seat.

5. The high flow volume nasal irrigation device of claim 1, wherein a compression of the valve seat is approximately 20 percent its uncompressed length.

6. The high flow volume nasal irrigation device of claim 1, wherein the valve seat and the spring store mechanical energy when in a compressed configuration and return the stored mechanical energy and momentarily reverse the fluid flow as the valve moves back to the standoffs in a recoil and restore configuration.

7. The high flow volume nasal irrigation device of claim 1, further comprising:
 a) a second reservoir of liquid located at a height above the first reservoir, the second reservoir configured to create an applied pressure from a volume of liquid at a predetermined height; and
 b) a conveyance tube configured to convey the liquid into the chamber and introduce an increase in pressure in the chamber.

8. A high flow volume nasal irrigation device, comprising:
 a) a squeeze bottle configured to elastically deform in response to a manually applied pressure on the bottle and thus pressurize a liquid and chamber therein, the squeeze bottle comprising an open end and an interior;
 b) a removable cap disposed on the squeeze bottle open end, the cap comprising a nipple configured to be inserted in a typical user's nostril, a nipple orifice and a nipple extension coaxial with the orifice;
 c) a tube configured to convey a liquid from a reservoir in the chamber under an elevated chamber pressure to a lower pressure outside the chamber, the tube comprising a free end and a housing at a second end adjoined to the cap with a coaxial cap nipple;
 d) a valve assembly proximal the tube inside the housing, the valve assembly comprising a disk-like valve and a plurality of housing standoffs configured to stop the valve but allow a fluid flow in the housing and out the cap nipple, an outer periphery of the valve and the housing forming an area for the fluid flow;
 e) a cylindrical elastic valve seat adjoined to the cap nipple and forming a gap with the valve on the standoffs, the valve seat having an inside diameter smaller than the valve and a restoring force in opposition to a force applied by the valve on the valve seat in response to a fluid pressure; and
 f) a spring configured to oppose the valve moving toward the valve seat from the standoffs and assist in returning the valve from the valve seat to the standoffs and thus with the valve seat create a periodic pulsatile fluid flow in the cap nipple in response to a chamber pressure which exceeds a critical chamber pressure threshold.

9. The high flow volume nasal irrigation device of claim 8, wherein a frequency of the pulsatile fluid flow is configurable as a function of an area of a fluid flow passage in the housing and out the cap nipple, the area and a mass of the disk, a valve seat spring rate and a spring rate of the spring.

10. The high flow volume nasal irrigation device of claim 8, wherein the valve comprises a nominal circumferential side wall and a top surface and a bottom surface, the top and bottom surfaces configured in at least one of a convex, a concave and a flat surface.

11. The high flow volume nasal irrigation device of claim 8, wherein the valve seat may be configured in a cylindrical bellows-like construction to facilitate oscillating motion and the pulsatile fluid flow through the nipple orifice.

12. The high flow volume nasal irrigation device of claim 8, wherein the tube, the housing, the valve and the elastic valve seat comprise at least one of an arcuate cross section and any polygonal cross section.

13. The high flow volume nasal irrigation device of claim 8, wherein the tube comprises a 6 mm (0.24 inches) nominal inside diameter and is no smaller than 3 mm (0.12 inches) inside diameter and no greater than 8 mm (0.32 inches) inside diameter.

14. A method of ejecting a high flow volume nasal irrigation rinse by manually squeezing a deformable nasal irrigation bottle containing a fluid and thereby creating a chamber pressure urging a fluid flow through a dip tube and out a bottle cap orifice placed into at least one of a user's nostrils, comprising:
 a) stopping fluid flow from the nasal irrigation bottle into the user's nostril by compressing a disk-like valve against a cylindrical elastic valve seat and a coaxial spring in response to a compressing force generated by a fluid pressure;
 b) restarting fluid flow from the nasal irrigation bottle into the user's nostril in response to a rebounding of the valve seat and spring and thus propelling the valve away from the valve seat toward a plurality of standoffs; and
 c) providing a pulsatile fluid flow through the nasal irrigation bottle cap orifice into the user's nostril, the pulsatile flow in response to the fluid flow stopping and restarting in a period related to a pressure threshold constant;
 the nasal irrigation bottle comprising:
 a squeeze bottle configured to elastically deform in response to a manually applied pressure on the bottle and thus pressurize the fluid and chamber therein, the squeeze bottle comprising an open end and an interior;
 a removable cap disposed on the squeeze bottle open end, the cap comprising a nipple configured to be inserted in a typical user's nostril, the bottle cap orifice and a nipple extension coaxial with the orifice;
 the dip tube configured to convey a fluid from a reservoir in the chamber under an elevated chamber pressure to a lower pressure outside the chamber, the tube comprising a free end and a housing at a second end adjoined to the cap with a coaxial cap nipple;
 a valve assembly proximal the tube inside the housing, the valve assembly comprising the disk-like valve and the plurality of standoffs configured to stop the valve but allow a fluid flow in the housing and out the cap nipple, an outer periphery of the valve and the housing forming an area for the fluid flow;
 the cylindrical elastic valve seat adjoined to the cap nipple and forming a gap with the valve on the standoffs, the valve seat having an inside diameter smaller than the valve and a restoring force in opposition to a force applied by the valve on the valve seat in response to a fluid pressure; and
 the spring configured to oppose the valve moving toward the valve seat from the standoffs and assist in returning the valve from the valve seat to the standoffs and thus with the valve seat create a periodic pulsatile fluid flow in the cap nipple in response to a chamber pressure which exceeds a critical chamber pressure threshold.

15. The method of ejecting a high flow volume nasal irrigation rinse of claim 14, wherein stopping fluid flow further comprises increasing a fluid pressure acting on the valve and compressing the valve into the valve seat.

16. The method of ejecting a high flow volume nasal irrigation rinse of claim 14, further comprising:
 a) squeezing the bottle gently to a chamber pressure below the pressure threshold constant to eject a continuous stream of the fluid from the bottle;
 b) squeezing the bottle vigorously to a chamber pressure above the pressure threshold constant to eject an oscillatory pulsating stream of the fluid from the bottle; and
 c) alternating between ejecting a continuous fluid stream and a pulsating fluid stream by alternating the respective gentle and vigorous squeezings.

17. The method of ejecting a high flow volume nasal irrigation rinse of claim 14, further comprising configuring the pressure threshold constant as a function of at least an area of a fluid flow passage through the tube and past the valve, the area and a mass of the valve and a spring installed force and a spring rate.

18. The method of ejecting a high flow volume nasal irrigation rinse of claim 14, further comprising varying the pressure threshold constant by varying at least one of an area of a fluid flow passage through the tube and past the valve, the area and a mass of the valve and a spring installed force and a spring rate.

19. The method of ejecting a high flow volume nasal irrigation rinse of claim 14, further comprising varying an oscillatory frequency and period of a pulsating stream of fluid ejected from the bottle by varying the manual pressure applied to the squeeze bottle.

* * * * *

UNITED STATES PATENT AND TRADEMARK OFFICE
CERTIFICATE OF CORRECTION

PATENT NO. : 8,366,681 B2  
APPLICATION NO. : 12/942634  
DATED : February 5, 2013  
INVENTOR(S) : Mark Carpenter Page 1 of 1

It is certified that error appears in the above-identified patent and that said Letters Patent is hereby corrected as shown below:

Title Page, insert

--(73) Assignee: Skylab Developments Inc., White Lake, MI (US)--

Signed and Sealed this  
Twenty-third Day of April, 2013

Teresa Stanek Rea  
*Acting Director of the United States Patent and Trademark Office*